Oct. 28, 1958 R. S. MOORE Plant Pat. 1,767

MINIATURE ROSE PLANT

Filed Dec. 27, 1957

WITNESS

Addison E. Avery

INVENTOR.

Ralph S. Moore

Webster & Webster

ATTYS.

United States Patent Office

Plant Pat. 1,767
Patented Oct. 28, 1958

1,767

MINIATURE ROSE PLANT

Ralph S. Moore, Visalia, Calif.

Application December 27, 1957, Serial No. 705,727

1 Claim. (Cl. 47—61)

This invention relates to a new and distinct variety of hybrid miniature rose plant, of bush type, originated by me in my nursery located at Visalia, California.

The variety is a cross between an unnamed seedling (Rosa Wichuriana × Floradora) as the seed parent, and another seedling (Carolyn Dean × Tom Thumb) as the pollen parent; such other seedling being known to me as "Zee," but which has not been introduced to the trade, as it is used by me only for breeding purposes. None of the above identified prior varieties are patented, except Tom Thumb (United States Plant Patent No. 169).

Subsequent to the origination by me of the herein claimed variety of miniature rose plant, and when it came into maturity and its distinctive features were recognized, I successfully asexually reproduced said variety—in my nursery located as aforesaid—by cuttings; such reproductions having been found, by careful observation, to run true in all respects.

The present variety is characterized by a plant which branches from close to the soil level, and is thick and bushy, with small, abundant foliage; reproduction being accomplished readily from soft wood cuttings.

The variety is further characterized by tiny buds which are soft pink and resemble the Cecil Brunner (unpatented), but are of considerably smaller size.

A further and very important distinctive characteristic of the variety resides in the flowers, which are very small in size, and pink in color when grown under conditions of cool weather and shelter—as in a greenhouse in the winter—but are substantially white when grown under conditions of warm weather and exposure to light—as outside in the summer and early fall. The petals are long, narrow, sometimes twisted, and curve outward and downward, giving the flowers the appearance of tiny Crego Aster (unpatented) blooms.

In general, the present variety will outbloom substantially all other miniature roses when grown as a pot plant, but the blooms are not extremely long lasting.

Figure 2:
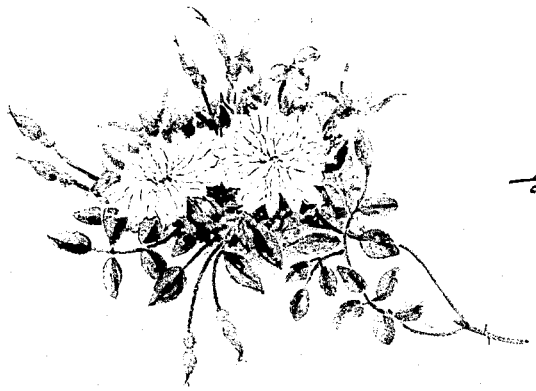
Fig. 2 is a similar view, but shows the flowers in the substantially white stage.
Figure 1:
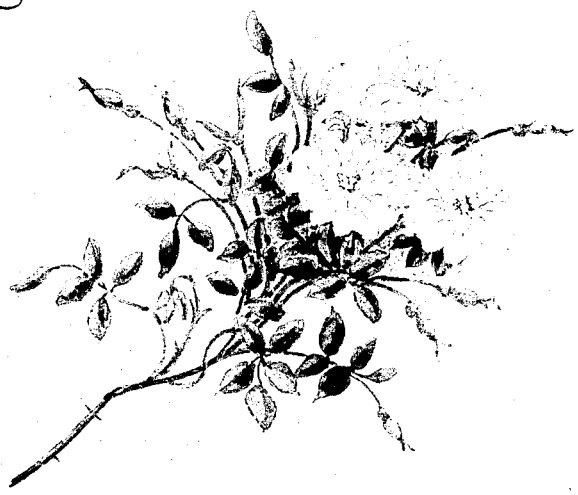
Fig. 1 is an elevation showing a spray, including stem, foliage, buds, and flowers in the pink stage.

Referring now specifically to the new and distinct variety of miniature rose plant, the following is a detailed description thereof in outline; all major color plate identifications being by reference to Maerz and Paul Dictionary of Color, except where common terms of color definition are employed.

Type: Dwarf; bush; seedling; greenhouse; outdoor; garden decoration potted plant.

Class: Miniature.

*Flowers*

Continuity: Continuous.

Fragrance: Moderate.

Flowers borne: Several to stem (two to three) in irregular pyramidal cluster on normal medium stems.

Quantity of bloom: Abundant, outdoors and in greenhouse.

Bud:

*Peduncle.*—Long; medium; erect; almost smooth. Color—medium green.

*Before calyx breaks.*—Size—small. Form—pointed, with foliaceous parts extending beyond the tip of the bud equal to one-quarter or more of its length. Color—green (21–L–5), with a bronze cast when grown outdoors.

*As calyx breaks.*—Color—very soft pink (1–E–1).

*As first petal opens.*—Size—small. Form—long; pointed. Color—soft pink (1–D–3 to 1–F–4).

Bloom:

*Size when fully open.*—Very small—averaging 1" to 1¼".

*Petalage.*—Double, with from forty to fifty petals on the average, arranged irregularly.

*Form.*—Full high center at first; petals initially and at maturity being loosely rolled outward. Nearly all the petals are very narrow, almost ribbon-like, and reflex to make the open flower look like a miniature Crego Aster.

Petals: Thin; soft; satiny (both sides).

*Shape.*—Outside — obovate. Intermediate — lanceolate. Inside—lanceolate.

*Color.*—Under conditions of cool weather and shelter, a soft pink (1–D–3 to 1–F–4). Under conditions of warm weather and exposure to light, substantially white (1–A–1), sometimes with the retention of a minimum of very pale pink (1–E–1). There is always a touch of yellow at the base of each petal.

*Behavior.*—Drops off cleanly in dry weather. Persists if weather is damp.

*Flower longevity.*—Bush in garden—average three days. Cut flowers kept at normal living room temperatures—two to three days.

*Reproductive Organs*

Stamens: Medium number; arranged irregularly; mixed with petaloids.

Filaments: Short; most with anthers; soft pale yellow.

Anthers: Small; All open at once; yellow.

Pollen: Abundant; lemon.

Pistils: Medium number.

Styles: Even; short; bunched.

Stigma: White to yellow.

Ovaries: All enclosed in calyx.

Hips: Ovoid; moderately smooth; walls thin and dry. Color—reddish brown.

Sepals: Spear shaped. Color—green.

Seeds: Few; small.

*Plant*

Foliage:

*Leaves.*—Compound of five leaflets; abundant; small; soft; glossy.

*Leaflets.*—Oval; apex acute; base round; margin serrate.

*Rachis.*—Medium. Upper side—grooved. Under side—average two to three weak thorns.

*Stipules.*—Short, with medium length points turning out at an angle of about 45 degrees.

*Color.*—Top side—medium green (22–L–10). Under side—somewhat lighter green (22–G–4). The under side of young leaves is shaded or tinted a bronze red.

Growth:

*Habit.*—Dwarf; bushy; much branched.

*Growth.*—Free; vigorous.

*Canes.*—Medium.

*Main stems.*—Color—green to bronze red. Thorns—several; hooked downward. Prickles—few. Hairs—none.

*Branches.*—Color—green to bronze red. Thorns—few to several; short; hooked downward; base short. Prickles—none. Hairs—none.

*New shoots.*—Color—green. Thorns—few; hooked downward; base short. Prickles—none. Hairs—none.

The miniature rose plant and its flowers as herein described may vary in slight detail due to climatic and soil conditions under which the variety may be grown.

The following is claimed:

A new and distinct variety of miniature rose plant of dwarf, bush type, substantially as described and illustrated, characterized by a small, free and vigorous growing, thick and very bushy, plant with small, abundant foliage; a plant which propagates readily from soft wood cuttings; a plant which blooms more profusely than most other miniature roses when grown as a pot plant; abundant flowers which are pink under conditions of cool weather and shelter, and substantially white under conditions of warm weather and exposure to light; and long, narrow, sometimes twisted petals which reflex outwardly and downwardly, giving the flowers the appearance of tiny Crego Asters.

No references cited.